United States Patent [19]
Edwards et al.

[11] Patent Number: 5,770,228
[45] Date of Patent: Jun. 23, 1998

[54] PLATELET DERIVED GROWTH FACTOR GEL FORMULATION

[75] Inventors: Martin W. Edwards, Woodinville, Wash.; Niels Christian Larsen, HvileBaekvaenge, Denmark

[73] Assignees: ZymoGenetics, Inc., Seattle, Wash.; Novo Nordisk A/S, Bagsvaerd, Denmark

[21] Appl. No.: 183,115

[22] Filed: Jan. 14, 1994

Related U.S. Application Data

[63] Continuation of Ser. No. 786,806, Nov. 4, 1991, abandoned.

[51] Int. Cl.[6] .............................. A61K 9/06; A61K 38/17
[52] U.S. Cl. .......................... 424/488; 424/78.02; 514/2; 514/21; 514/944
[58] Field of Search ..................................... 424/484, 488, 424/78.02, 494, 78.08, 94.1, 445, 449; 514/944

[56] References Cited

U.S. PATENT DOCUMENTS

| | | | |
|---|---|---|---|
| 4,717,717 | 1/1988 | Finkenaur | 514/21 |
| 4,845,075 | 7/1989 | Murray et al. | 514/12 |
| 4,861,757 | 8/1989 | Antoniades et al. | 514/21 |
| 5,045,601 | 9/1991 | Capelli et al. | 424/445 |
| 5,093,133 | 3/1992 | Wisniewski | 424/484 |
| 5,120,546 | 6/1992 | Hansen et al. | 424/449 |
| 5,124,316 | 6/1992 | Antoniades et al. | 514/12 |
| 5,409,896 | 4/1995 | Ammann et al. | 514/13 |
| 5,427,778 | 6/1995 | Finkenaus et al. | 424/78.08 |
| 5,457,093 | 10/1995 | Cini et al. | 514/12 |
| 5,464,387 | 11/1995 | Haak et al. | 604/20 |

FOREIGN PATENT DOCUMENTS

| | | |
|---|---|---|
| 267015 | 5/1988 | European Pat. Off. . |
| 282317 | 9/1988 | European Pat. Off. . |
| 312208 | 4/1989 | European Pat. Off. . |
| 88/03409 | 5/1988 | WIPO . |
| 89/05656 | 6/1989 | WIPO . |

*Primary Examiner*—Raj Bawa
*Attorney, Agent, or Firm*—Townsend and Townsend and Crew

[57] ABSTRACT

Therapeutic compositions comprising a therapeutically effective amount of platelet derived growth factor in a hydroxyethyl cellulose gel are provided. These compositions may include a preservative, such as methyl paraben. These compositions may also include ethanol.

22 Claims, 1 Drawing Sheet

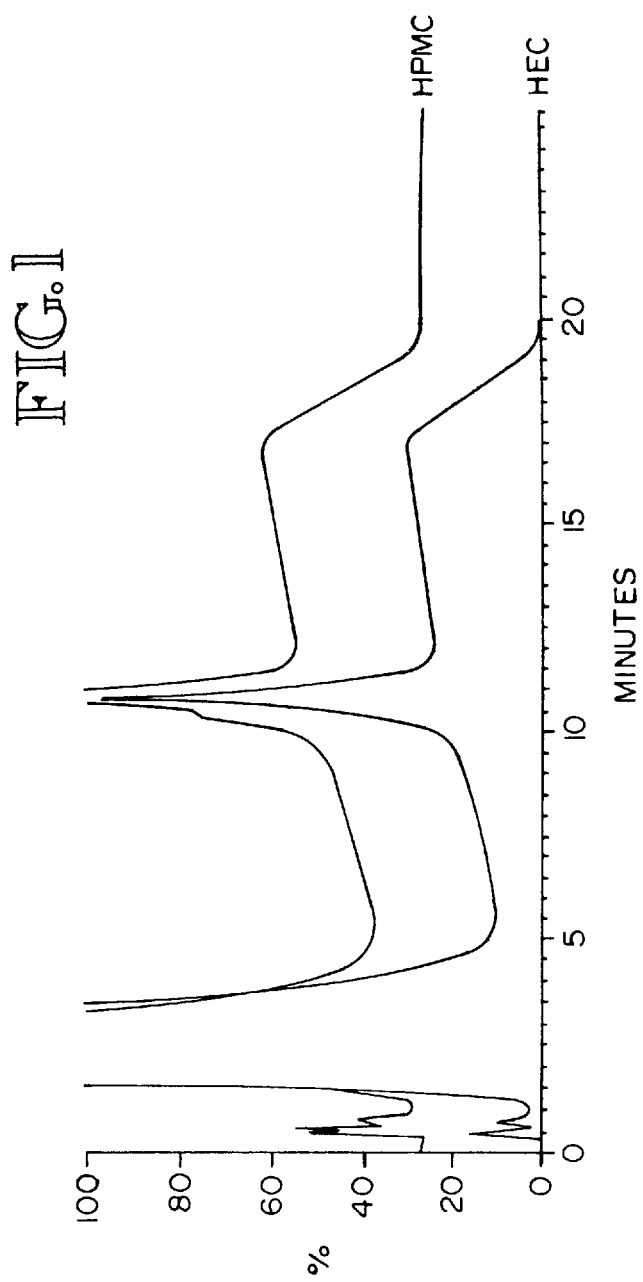

PLATELET DERIVED GROWTH FACTOR
GEL FORMULATION

CROSS-REFERENCE TO RELATED
APPLICATION

This application is a continuation of U.S. patent application Ser. No. 07/786,806, filed Nov. 4, 1991, now abandoned.

TECHNICAL FIELD

The present invention relates generally to platelet derived growth factor (PDGF) and PDGF analogs, and more specifically, to compositions of PDGF which have been formulated in a gel for therapeutic use.

BACKGROUND OF THE INVENTION

Human platelet-derived growth factor (PDGF) has been shown to be the major mitogenic protein in serum for mesenchymal derived cells. This is well documented by numerous studies of platelet extracts or purified PDGF induction of either cell multiplication or DNA synthesis (a prerequisite for cell division) in cultured smooth muscle cells, fibroblasts and glial cells (Ross et al., *PNAS* 71:1207, 1974; Kohler and Lipton, *Exp. Cell Res.* 87:297, 1974; Westermark and Wasteson, *Exp. Cell Res.* 98:170, 1976; Heldin et al., *J. Cell Physiol.* 105:235, 1980; Raines and Ross, *J. Biol. Chem.* 257:5154, 1982). Furthermore, PDGF is a potent chemoattractant for cells that are responsive to it as a mitogen (Grotendorst et al., *J. Cell Physiol.* 113:261, 1982; Seppa et al., *J. Cell Biol.* 92:584, 1982). This is somewhat unusual in that mitogens generally do not also act as chemotactic agents.

PDGF has therapeutic applications for the treatment of injuries which require the proliferation of fibroblasts or smooth muscle cells to heal. More specifically, in vivo, PDGF normally circulates stored in the alpha granules of platelets. Injury to arterial endothelial linings causes platelets to adhere to the exposed connective tissue and release their granules. In this regard, PDGF has been shown to be active in promoting wound healing in several animal models. For instance, Lynch et al. (*Proc. Natl. Acad. Sci. USA* 84:7696–7700, 1987) disclose the use of insulin-like growth factor I (IGF-1) and purified PDGF to promote wound healing. The two growth factors showed a synergistic effect in promoting the healing of dermal wounds in pigs. Lynch et al. (*J. Clin. Periodontol.* 16:545–548, 1989) also found that a combination of PDGF and IGF-1 promotes bone and cementum formation in a dog model of periodontitis. In addition, Greenhalgh et al. (*Am. J. Pathol.* 136:1235–1246, 1990) demonstrated enhanced healing of full-thickness skin wounds in genetically diabetic mice treated with recombinant PDGF as compared to control animals. Finally, Thomason et al. (European Patent Office Publication 282,317 A2) disclose that recombinant PDGF accelerates the gain in tensile strength of healing skin wounds in rats and promotes wound healing in diabetic rats.

However, commercially preferred delivery systems for the topical administration of PDGF have not previously been available. This has been due in part to the fact that PDGF is sensitive to proteolysis (Hart et al., *Biochemistry* 29:166–172, 1990; U.S. Ser. No. 07/557,219). In addition, it has been found by the inventors that highly purified PDGF exhibits instability when formulated for use as a topical therapeutic agent. For example, certain conventional gels, such as methyl cellulose and hydroxypropylmethyl cellulose, and certain conventional preservatives, such as benzyl alcohol, are incompatible with PDGF.

Thus, there is a need in the art for therapeutic compositions of PDGF which are suitable for topical administration, and which are also stable in long-term storage. The present invention provides such compositions and also provides other related advantages.

SUMMARY OF THE INVENTION

Briefly stated, the present invention provides compositions comprising a therapeutically effective amount of PDGF in a hydroxyethyl cellulose gel. Within the context of the present invention, PDGF will be understood to include the AA, BB and AB isoforms of PDGF, individually or in combination, as well as analogs thereof. In addition, the BB isoform of PDGF is also understood to encompass the viral homolog (the v-sis gene product). PDGF may be obtained from either recombinant or native sources.

Within a preferred embodiment, the PDGF is PDGF-BB, particularly recombinant human PDGF-BB. A preferred concentration in this regard is from about 5 $\mu$g to about 5 mg per gram of gel, with from about 50 $\mu$g to about 500 $\mu$g per gram of gel being particularly preferred.

Within another aspect of the present invention the composition also comprises a preservative, such as methyl paraben (also known as methyl parahydroxybenzoate). Within certain embodiments, it is preferable to provide the methyl paraben at a concentration of about 0.05% to about 1.0%, with about 0.1% to 0.2% being particularly preferred.

Within yet another aspect of the present invention the composition also comprises ethanol.

Within each of the embodiments of the present invention briefly described above, it is preferable to provide a concentration of hydroxyethyl cellulose in the gel of from about 1% to 5%.

Within a related aspect of the present invention, a method of promoting wound healing in warm-blooded animals is provided, comprising administering to the animal a therapeutically effective amount of a composition as discussed above.

These and other aspects of the invention will become evident upon reference to the following detailed description and attached drawing.

BRIEF DESCRIPTION OF THE DRAWING

The FIGURE illustrates elution profiles of PDGF-BB after storage in hydroxypropylmethyl cellulose (HPMC) and hydroxyethyl cellulose (HEC) gels.

DETAILED DESCRIPTION OF THE INVENTION

The present invention provides compositions comprising a therapeutically effective amount of PDGF in a hydroxyethyl cellulose gel. As noted above, PDGF may be obtained from native sources or produced using recombinant DNA techniques. Methods for producing recombinant PDGF and PDGF analogs are described within U.S. Pat. Nos. 4,769,322; 4,801,542; and 4,766,073 and within EP 282,317, which are hereby incorporated by reference in their entirety. PDGF may also be produced in bacteria (See Tackney et al., WO 90/04035). Methods for purifying PDGF from native sources are described by Raines and Ross (*J. Biol. Chem.* 257:5154–5160, 1982), Hart et al. (*Biochemistry* 29:166–172, 1990), and in U.S. Pat. No. 4,479,896.

As discussed in certain of the issued patents noted above, it has been found that by utilizing the secretory pathway of eucaryotic cells to express PDGF, biologically active material may be obtained. Expression and secretion of the appropriate gene product from eucaryotic cells enables proper processing and assembly, resulting in molecules with a native and biologically active conformation. In the alternative, PDGF polypeptide chains may be expressed in procaryotic cells, isolated, and assembled in vitro to produce biologically active molecules.

The biological activities of PDGF include inducing chemotaxis and/or mitogenesis of responsive cell types, following the binding of PDGF to specific cell surface receptors. Other biological effects of PDGF may include: phospholipase activation; increased phosphatidylinositol turnover and prostaglandin metabolism; stimulation of both collagen and collagenase synthesis by responsive cells; an indirect proliferative response of cells lacking PDGF receptors; and potent vasoconstrictor activity.

In general, the secretory pathways of eucaryotes are believed to be quite similar. For example, mammalian cell and yeast cell secretory pathways are well characterized and are known to be homologous. The presence of a secretory signal sequence on the expressed polypeptide is an important element in eucaryotes, due to its role in directing the primary translation product into the secretory pathway, thereby leading to proper processing and assembly. Provided that appropriate transcriptional promoter and secretory signal sequences are utilized, generally any eucaryotic cell can express and secrete PDGF in a biologically active form for use within the present invention. An easily manipulable and well-characterized eucaryotic cell is the yeast cell.

For expression in yeast, a DNA sequence encoding a PDGF polypeptide is ligated to an appropriate promoter and secretory signal sequence. Promoters which may be utilized in yeast include the yeast alpha-factor (MFα1) promoter and the yeast triose phosphate isomerase (TPI1) promoter. Promoters may also be obtained from other yeast genes, e.g., alcohol dehydrogenase 1 (ADH1), alcohol dehydrogenase 2 (ADH2). Appropriate promoters for other eucaryotic species may also be used and will be apparent to those skilled in the art. Secretion of the PDGF gene products may be accomplished through use of the prepro secretory signal sequence of the yeast mating pheromone alpha-factor (Kurjan and Herskowitz, *Cell* 30:933, 1982; Julius et al., *Cell* 36:309, 1984; and Brake et al., *PNAS* 81:4642, 1984), or the yeast BAR1 gene leader and third domain sequences (see U.S. Pat. No. 5,037,743), although other secretion signals may be used. To ensure the efficient transcription termination and polyadenylation of mRNA, a yeast terminator sequence, such as the triose phosphate isomerase terminator, may be added (Alber and Kawasaki, *J. Molec. Genet. Appl.* 1:419, 1982.) Methods of ligation of DNA fragments have been amply described (Sambrook et al., *Molecular Cloning: A Laboratory Manual*, 2nd Edition, Cold Spring Harbor Laboratory, 1989) and are well within the skill of those of ordinary skill in the art to perform. After preparation of the expression unit constructions, the constructs are inserted into an appropriate expression vector.

It is preferable to use an expression vector which is stably maintained within the host cell in order to produce more biological activity per culture. Suitable yeast expression vectors in this regard are the plasmids pCPOT (ATCC 39685) and pMPOT2 (ATCC 67788), which include the *Schizosaccharomyces pombe* gene encoding the glycolytic enzyme triose phosphate isomerase (POT1 gene). Inclusion of the POT1 gene ensures the stable maintenance of the plasmid in a host cell having a TPI gene deletion due to its ability to complement the gene deletion in the host cell.

After preparation of a DNA construct incorporating the POT1 selectable marker and an expression unit comprising, for example, the TPI1 promoter, the BAR1 leader and third domain sequences, an appropriate DNA sequence encoding PDGF, and the TPI1 terminator, the construct is transformed into a yeast host with a TPI1 gene deletion. Procedures for transforming yeast are well known in the literature.

The transformed yeast cells may be selected by growth on a conventional complex medium containing glucose when the POT1 gene is utilized as a selectable marker. A conventional medium, such as YEPD (20 grams glucose, 20 grams Bacto-peptone, 10 grams yeast extract per liter), may be used. Once selected, transformants containing the appropriate expression constructions are grown to stationary phase on conventional complex media, the cells removed by centrifugation or filtration, and the medium concentrated. Since PDGF is a highly cationic and hydrophobic protein (Raines and Ross, ibid.; Antoniades, *PNAS* 78:7314, 1981; Deuel et al. *J. Biol. Chem.* 256:8896 1981), recombinant PDGF similarly possesses characteristics which allow the use of ion exchange chromatography in its purification. For example, recombinant PDGF-BB in yeast fermentation broth is separated from the cells and fractionated by cation exchange chromatography. PDGF-BB desorbed from the column is acidified and further fractionated by reverse phase chromatography under batch conditions. The PDGF-containing effluent is acidified and passed through a strong cation exchange column and eluted with a NaCl step gradient. The effluent is collected, and PDGF-BB is precipitated using $(NH_4)_2SO_4$. The resulting material is desalted by gel filtration and separated according to charge. The effluent is acidified and applied to a strong cation exchange column and eluted with a linear gradient of $NH_4HCO_3$ at pH 8–10. The effluent is collected, and PDGF-BB is precipitated by the addition of $(NH_4)_2SO_4$. The resulting precipitate is dissolved in acetic acid and fractionated by gel filtration. The effluent is desalted and freeze dried.

Using a variety of assays, it can be demonstrated that recombinant PDGF from yeast cultures possesses biological activities substantially identical to native human PDGF.

Expression of biologically active proteins in eucaryotic cells other than yeast cells can be achieved by a person skilled in the art through use of appropriate expression/regulatory signals. Transcriptional promoters capable of directing the expression of PDGF sequences are chosen for their ability to give efficient and/or regulated expression in the particular eucaryotic cell type. Signal sequences capable of directing the gene product into the cell's secretory pathway are chosen for their function in the host cell. The selection of other useful regulatory signals, such as transcription termination signals, polyadenylation signals and transcriptional enhancer sequences, would be apparent to an individual skilled in the art.

Recombinant PDGF has been shown to possess substantially the same biological activity as native PDGF. The basic biological activity of PDGF, particularly the induction of chemotaxis and mitogenesis in responsive cell types (including fibroblasts and smooth muscle cells), underlies many of the physiological roles of this protein, including its role in tissue repair.

The normal wound-healing process in warm-blooded animals proceeds by an orderly series of events involving the interaction of chemoattractants, growth factors, and a variety of specialized cell types. This process includes an ordered migration and, in some cases, the subsequent proliferation of a number of these specialized cell types into the wound space, and involves the complex interaction of a variety of biologically active factors. This process is discussed in detail in Hunt et al. (eds.), *Soft and Hard Tissue Repair; Biological and Clinical Aspects*, Praeger Publishers, New York, 1984, which is hereby incorporated by reference. Briefly, tissue injury results in the release of chemotactic factors which attract particular cell types, which then release additional and/or other chemoattractant or mitogenic factors. These factors, in turn, affect additional specialized cells, ultimately restoring the injured tissue. Further, there is evidence that the rate at which this process normally proceeds is limited by the levels of chemoattractants and growth factors at the wound site, and may be enhanced by the addition of these agents (Grotendorst et al., *J. Clin. Invest.* 76:2323–2329, 1985, herein incorporated by reference).

The wound-healing process in the dermis begins with the formation of a clot from the blood which flows into the wound. This results in a cross-linked network of fibrin molecules binding the wound together. During this process, platelets adhere to the injured tissue, becoming activated, and release the contents of their alpha granules. The disruption of the dermal tissue, the blood coagulation reactions, and platelet activation all generate molecules which cause the migration of a series of new cells into the wound, thereby initiating the repair process.

Among the contents of the alpha granules released by the platelets is PDGF. In addition, other contents of the alpha granules and by-products of the coagulation reactions induce the appearance of macrophages. Macrophages are a second important source of PDGF in the wound. The deposition of PDGF at the site of an injury provides a chemotactic stimulus for fibroblasts to enter the wound space and a mitogenic stimulus for the fibroblasts to subsequently proliferate therein, thereby participating in the process of repair. An important role of the fibroblast is regeneration of connective tissue at the wound site. The fibroblasts proliferate in the wound and deposit collagen types I and II and other extracellular proteins to the connective tissue matrix. The presence of new fibroblasts and their protein products reconstitutes the dermal architecture such that it can be re-epithelialized and the wound thereby healed.

Similarly, the wound-healing process in relation to the repair of connective tissue also requires fibroblast infiltration and proliferation, leading to subsequent collagen deposition.

Because the chemotactic and mitogenic properties of PDGF are central to its role in the wound-healing process, it has substantial therapeutic utility in the treatment of wounds in which healing requires the migration and/or proliferation of fibroblasts. In addition, PDGF acts as a chemotactic and mitogenic agent for smooth muscle cells, the proliferation of which may contribute to the healing of certain wounds. Smooth muscle cells will be affected by PDGF in a manner similar to that described above for fibroblasts, thereby contributing to the healing process.

PDGF is particularly useful in individuals who have substantially impaired wound healing capacity, and thereby lack the ability to provide to the wound site endogenous growth factors which are necessary for the process of wound healing. In these individuals, the addition of exogenous proteins having the biological activity of PDGF enables wound healing to proceed in a normal manner. Normal wound-healing may be retarded by a number of factors, including advanced age, diabetes, cancer, and treatment with anti-inflammatory drugs or anticoagulants, and thus the therapeutic activity of PDGF may be used to offset the delayed wound-healing effects of such treatments.

PDGF accelerates the healing process in a broad spectrum of wound conditions. For purposes of the present invention, the terms "wound" or "wound condition" include any disruption of the dermal layer of the skin. Examples of disruptions to the dermal layer include chronic non-healing dermal ulcers (which can have a variety of causes), superficial wounds and lacerations, abrasions, surgical wounds, and some burns. In addition, wounds may also result in damage to connective tissue, the repair of which involves fibroblast proliferation and collagen deposition. The compositions of the present invention are useful in enhancing the healing process of all of these wounds, and will also be useful in the treatment of other wounds in which healing requires the migration and/or proliferation of fibroblasts. Wounds in hard tissue can also be treated with the compositions of the present invention. For example, bone chips may be added to a PDGF gel formulation and the resultant mixture used to fill a bone defect. The PDGF stimulates formation of new bone at the site of the defect.

As noted above, the present invention provides compositions comprising a therapeutically effective amount of PDGF in a hydroxyethyl cellulose gel. Briefly, hydroxyethyl cellulose (HEC) is obtained as a dry powder which is reconstituted in water or an aqueous buffer solution to give the desired viscosity (generally about 200 cps to 30,000 cps, corresponding to about 0.2–10% HEC). A preferred concentration of HEC is between 1% and 5%, more preferably 1%–2%, and most preferably 1.5%. Filter sterilized PDGF is then added, and the mixture is stirred. Preferred buffers include acetate and citrate at slightly acidic pH. Particularly preferred buffers are sodium acetate buffer at pH 4.5–6.5, most preferably 100 mM acetate at pH 5.5 and citrate buffer at pH 6.0–6.5. It is also preferred to include a preservative (antimicrobial agent) within the above-described composition. A preferred preservative is methyl paraben. It is preferred to provide methyl paraben at a concentration of about 0.05% to about 1.0%, with about 0.1% to 0.2% being particularly preferred. Within a preferred embodiment, the gel is prepared by mixing water, methylparaben, hydroxyethylcellulose and sodium acetate. The mixture is sterilized by autoclaving at 120° C. for 20 minutes, and tested for pH, methylparaben concentration and viscosity before mixing with the appropriate amount of PDGF.

PDGF which is utilized within the present invention is preferably substantially pure, that is, generally free of impurities or contaminants which would interfere with its therapeutic use. Particularly preferred are those preparations which are free of toxic, antigenic, inflammatory or other deleterious substances, and are greater than 90%, preferably greater than 99%, pure. As used within the context of the present invention, a "therapeutically effective amount" is that amount of PDGF which is sufficient to produce a statistically significant increase in the rate of healing as determined by standard histological measurements or wound contraction rates. Typically, PDGF is utilized at a concentration of about 5 $\mu$g to 5 mg per gram of gel, and preferably at a concentration of about 50–500 $\mu$g per gram of gel.

As noted above, the compositions of the present invention may be utilized to promote wound healing in warm-blooded animals. Briefly, these compositions are typically administered topically in a therapeutically effective amount, depending of course on the size and characteristics of the wound. In general, about 0.1 ml to 0.5 ml of gel will be applied per $cm^2$ of wound area. The gel will be formulated to provide about 5 $\mu$g to 250 $\mu$g of PDGF per $cm^2$ of wound area. The compositions may be reapplied at one- to several-day intervals until healing is complete.

The therapeutic compositions of the present invention may also contain other pharmaceutically active ingredients, for example, heparin, which has been shown to accelerate the healing of thermal burns. Other growth factors, such as TGF-α, TGF-β, EGF, basic or acidic FGF, platelet factor 4, insulin or somatomedins (see Grotendorst et al., 1985) and angiogenesis factor, may also work synergistically with PDGF as described herein. Antibiotics may also be included to keep the wound free of infection.

In addition, as noted above, the compositions of the present invention may also include ethanol. Ethanol is included to reduce the dielectric constant of the preparation, thereby increasing protein stability. Preliminary data indicates that 1% ethanol is preferable to 10% ethanol, both of which are preferable to 0% ethanol. Glycerol or propanol may also be suitable.

The following examples are offered by way of illustration and not by way of limitation. It will be appreciated by those skilled in the art that the gel formulations discussed within the examples may be used with all isoforms and analogs of PDGF.

EXAMPLE 1

Efficacy of Methyl Paraben and Benzyl Alcohol as Preservatives

Methyl paraben and benzyl alcohol were tested in order to determine their efficacy as preservatives of the BB isoform of platelet derived growth factor (PDGF-BB). PDGF-BB at 50 μg/ml and 500 μg/ml was dissolved in a solution of purified water and either 0.2% methyl paraben or 1% benzyl alcohol. The solutions were held at 40° C. in 10 ml siliconized vials and sampled after 1 and 2 weeks. The concentration of PDGF-BB was analyzed by cation exchange HPLC on a 50 mm×7.8 mm Bio-Rad HPLC MA7S Cation Exchange Column (Bio-Rad, Richmond, Calif.). A linear gradient of Buffer A (0.05M NaCl, 30% $CH_3CN$, pH 2.0) and Buffer B (1.0M NaCl, 30% $CH_3CN$, pH 2.0), at a flow rate of 2.0 ml/min., went from 25% to 90% Buffer B in 15 minutes. Detection was at 214 nm. All solutions were at ambient temperature.

An examination of the relationship between peak area and width indicated significant decomposition of PDGF-BB in the benzyl alcohol preparations (Table 1). After 2 weeks at 40° C. a 25% and 10% decrease in the amount of PDGF-BB was seen in the 50 μg/ml and 500 μg/ml preparations, respectively. No such degradation was seen in the methyl paraben preparations, indicating its compatibility as a preservative in PDGF-BB formulations.

TABLE 1

Stability of PDGF-BB in preservatives

| Labeled PDGF-BB (μg/ml) | Weeks of Storage | PDGF-BB-% of Initial Amount | Area/peak Width-% of Starting Material | Comments |
|---|---|---|---|---|
| Benzyl Alcohol 1% | | | | |
| 50 | 0 | 100.000 | 100.000 | |
| 50 | 1 | 105.411 | 71.453 | Very broad peak |
| 50 | 2 | 106.710 | 76.824 | Very broad and low peak |
| 500 | 0 | 100.000 | 100.000 | |

TABLE 1-continued

Stability of PDGF-BB in preservatives

| Labeled PDGF-BB (μg/ml) | Weeks of Storage | PDGF-BB-% of Initial Amount | Area/peak Width-% of Starting Material | Comments |
|---|---|---|---|---|
| 500 | 1 | 95.266 | 93.000 | |
| 500 | 2 | 100.129 | 91.231 | Broad peak |
| Methyl paraben 0.2% | | | | |
| 50 | 0 | 100.000 | 100.000 | |
| 50 | 1 | 102.961 | 107.824 | |
| 50 | 2 | 105.011 | 105.047 | |
| 500 | 0 | 100.000 | 100.000 | |
| 500 | 1 | 101.858 | 119.281 | |
| 500 | 2 | 102.483 | 110.539 | |

EXAMPLE 2

Stability of PDGF-BB in HEC and HPMC E4M

The stability of PDGF-BB in hydroxyethyl cellulose (HEC) (Merck, Darmstadt, Germany) and in hydroxypropylmethyl cellulose (HPMC E4M) (Dow Chemical Europe, Switzerland) gels was investigated. Three sets of gels, containing 2 gels per set, were made with 50, 500 and 1000 μg/g of PDGF-BB. Each gel contained 10 mM acetate pH 5.5 and 0.2% methyl paraben in a 2.5% HPMC E4M gel. 500 μg/g and 1000 μg/g PDGF-BB gels which contained 1% HEC in place of the HPMC E4M were also made. The 50 μg/g PDGF-BB gels were stored in syringes (syringe product no. 391593-001; plungers 391592-001, Becton-Dickinson, Rutherford, N.J.) for 2 weeks at 30° C. and 40° C. while the gels containing 500 and 1000 μg/g of PDGF-BB were stored in test tubes for 4 weeks at 40° C. The amount of PDGF-BB was analyzed by cation exchange HPLC as described in Example 1.

Substantial derivitization of the 500 μg/g PDGF-BB samples was seen after a two-week incubation in the HPMC E4M gels (see FIGURE), while very little degradation was apparent in the samples incubated for 4 weeks in the HEC gel. Derivitization was not due to incubation within the syringes as derivitization also occurred within test tubes containing the HPMC E4M gels. In contrast, virtually no derivitization occurred to PDGF-BB in the HEC gel, thereby demonstrating its advantage over HPMC E4M as a gelling agent.

EXAMPLE 3

Stability of PDGF-BB in Methyl Cellulose

The stability of PDGF-BB in methyl cellulose gel was tested in an experiment similar to that described above in Example 1. Briefly, a methyl cellulose gel containing 50 μg/mg PDGF-BB was prepared and stored for four weeks at 30° C. and 40° C. Analysis by cation exchange chromatography as described in Example 1 showed a shoulder on the trace similar to that seen with HPMC gels (see FIGURE), indicating that significant derivitization of the PDGF had occurred.

EXAMPLE 4

Stability of PDGF-BB in Various Buffers

A study was made of the stability of PDGF-BB in acetate, citrate and phosphate buffers of varying pH and ionic strengths. One hundred millimolar stock solutions of pH 4.5, 5.5 and 6.5 (±0.1) were made of sodium dihydrogenphosphate (Merck, Darmstadt, Germany, art. no. 6346), trisodium citrate (Merck, art. no. 6448) and sodium acetate (Merck, art. no. 6267). These stock solutions were further diluted to concentrations of 10 mM and 1 mM and, if necessary, their pH was adjusted. Finally, PDGF-BB was dissolved into each solution to a concentration of 100 μg/ml, and the solutions were stored as 1 ml aliquots in 10 ml pre-siliconized vials. Solutions were held at 40° C. until sampling. The concentration of PDGF-BB was analyzed by cation exchange HPLC as described in Example 1. The pH was measured potentiometrically.

A nested factorial design was used in this study whereby the factors of pH, ionic strength and sampling time were nested within the 3 types of buffer systems. Initial pH and ionic strengths were tested at three levels, while sampling time was tested at 5 levels (0, 1, 2, 3 and 4 weeks). The effects on independent variables of PDGF-BB concentration and measured pH were tested in a general linear model (GLM) using a pairwise t-test to group the effects of the factors. Each buffer system was studied independently of the others.

Acetate System:

The interaction between ionic strength and initial pH had a significant influence on the final pH of the incubated sample (p<0.01) but not on the degradation of PDGF-BB (p<0.1). When the data were grouped by ionic strength and initial pH, PDGF-BB concentration, with one exception, decreased to 98% to 99% (SD<0.2) of its initial levels. The exception was in the combination of pH 6.5 and 1 mM ionic strength wherein the PDGF-BB concentration dropped to 83% of its initial value. A system with a pH adjusted to 6.5 is expected to be of significantly poorer stability since the $pK_a$ for acetate is 4.76, giving a pH range for optimal buffer capacity of 3.8 to 5.8. Accordingly, outside the buffer range, PDGF-BB degradation increased several fold.

The zero-order rate constant of PDGF-BB at 40°, $k_0$, was calculated for each combination of ionic strength and adjusted pH. Although the data are to be taken with care due to the insufficient separation of PDGF-BB and its derivatives, the data suggest that the greatest stability is obtained at high ionic strength and low pH. This result can be explained by virtue of the low $pK_a$ of acetate and hence its correspondingly low optimal buffering range as described above.

A comparison of the zero-order rate constants for degradation of PDGF-BB in the acetate system at varying pH and ionic strengths (Table 2) indicates that stability, as measured by $k_0$, increased significantly at pH 4.5 and 100 mM acetate.

Citrate System:

The interaction between ionic strength and initial pH had a significant influence on the final pH and the PDGF-BB concentration (p<0.01). A comparison of $k_0$ at 40° C. versus ionic strength and final pH illustrates the greatest stability at high pH and low ionic strength (Table 2). Furthermore, $k_0$ decreases with increasing pH and with decreasing ionic strength, giving an optimal stability in 1 mM citrate at pH 6.5. The citrate system, with an optimal pH and ionic strength close to physiological conditions, is particularly promising as a buffer for a PDGF-BB gel formulation.

Phosphate System:

The interaction between ionic strength and initial pH significantly influenced the final pH (p<0.01). The final pH was the only parameter that had significant effect on PDGF-BB degradation (p<0.01). The stability of PDGF-BB decreased with increasing pH (Table 2). Since the $pK_a$'s of phosphate are 2.15, 7.20 and 12.33 it is likely that proton activity, and not system buffer capacity, is responsible for PDGF-BB instability. Degradation of PDGF-BB may be due to deamidation which is prevented by protonization of amino groups a low pH. This hypothesis is strongly supported by the data.

TABLE 2

| Ionic Strength | Adjusted pH | Zero-order Rate-Constant (percent/week) | | |
|---|---|---|---|---|
| | | Acetate | Citrate | Phosphate |
| 1 | 4.5 | 0.923 | 0.000 | 0.000 |
| 1 | 5.5 | 0.602 | 0.000 | 0.000 |
| 1 | 6.5 | 12.333 | 0.000 | 0.724 |
| 10 | 4.5 | 0.550 | 3.571 | 0.000 |
| 10 | 5.5 | 0.641 | 3.302 | 1.267 |
| 10 | 6.5 | 1.015 | 0.000 | 1.174 |
| 100 | 4.5 | 0.000 | 6.898 | 0.474 |
| 100 | 5.5 | 0.575 | 4.465 | 1.483 |
| 100 | 6.5 | 0.822 | 0.000 | 2.163 |

EXAMPLE 5

Prediction of Shelf Life of PDGF-BB

A study was made to predict the shelf life of PDGF-BB formulations at 4° C. Briefly, PDGF-BB was formulated into an acetate buffered hydroxyethyl cellulose gel (HEC) containing methyl paraben as a preservative. The samples were held for 8 weeks at temperatures of 4°, 15°, 25°, 30° and 40° C. Stability was determined as a function of mitogenic activity and supported by quantitative PDGF-BB determination by size exclusion chromatography (SEC) and ion exchange chromatography (IEC). Additionally, gel viscosity, gel pH and methyl paraben concentration were followed.

PDGF-BB at three concentrations, 10, 100 and 1000 μg/ml, was formulated into 1.6% (w/v) HEC gels containing 0.2% (w/v) methyl paraben and 0.68% (w/v) sodium acetate. The samples were pH adjusted to 5.5 with HCl and stored as 1 ml aliquots in syringes (product no. 391593-001; plungers, no. 391592-001, Becton-Dickinson).

Concentrations of PDGF-BB derivatives were made by cation exchange HPLC as described in Example 1. Determination of the concentrations of PDGF-BB and its polymers was made by size exclusion chromatography (SEC).

SEC was performed on a Superdex™ 75 HR 10/30, 10×300–310 mm column (Pharmacia; Uppsala, Sweden). The sample to be tested was dissolved in 0.01M acetic acid or in eluant solution (13.8 g $Na_2H_2PO_4 \cdot H_2O$, 105.7 g $(NH_4)_2SO_4$, 200 μl triethanolamine, 80 g acetonitrile in $H_2O$, final volume 2 liters, pH adjusted to 7.0 with 4N NaOH, filtered through a 0.45 μm filter) to a concentration of 1 mg/ml PDGF. The resulting PDGF solution was kept below 10° C. prior to fractionation. The separation was run at room temperature using the eluant solution at a flow rate of 0.5 ml/minute, 50 μl injection volume, isocratic elution and a run time of 40 minutes. Detection was at 214 nm, AUFS=0.05. Percent high molecular weight components was calculated as:

%HMW=peak area before main peak/total peak area×100%

Samples held at 4° C. were tested at 0 and 8 weeks. Samples held at 15° C. were tested at 4 and 8 weeks.

Samples held at 25° C. were tested at 4 and 8 weeks. Samples held at 30° C. and 40° C. were tested at 2, 4, 6 and 8 weeks.

The appearance of the gel was determined macroscopically, pH was determined potentiometrically and rheology was determined viscosiometrically according to a second testing schedule. In this schedule, samples held at 4° C. were examined for the above three characteristics at 0 and 8 weeks. Samples held at 15° C. were tested at 8 weeks. Samples held at 20° C. were tested at 4 and 8 weeks. Samples held at 30° C. and 40° C. were tested at 4, 6 and 8 weeks.

Bioactivity of PDGF was analyzed by measuring PDGF BB-stimulated DNA synthesis in Swiss 3T3 fibroblasts as detected by the incorporation of [methyl-$^3$H]Thymidine. The cells were maintained in DMEM (GIBCO BRL, Grand Island, N.Y.) containing 10% heat-inactivated fetal calf serum (FCS; Hyclone, Lund, Sweden), 2 mM sodium pyruvate and 1% penicillin-streptomycin (GIBCO BRL) (DMEM/5% FCS) at 37° C. in a 5% $CO_2$ atmosphere in $T_{80}$ tissue culture flasks (Nunc, Roskilde, Denmark). The medium was changed every two to three days. Sub-confluent cells were washed with 2 ml/flask of trypsin-EDTA (GIBCO BRL). The cells were removed from the flasks with an additional 2 ml/flask of trypsin-EDTA. The cells were then diluted to $6 \times 10^4$ cells/ml with DMEM/5% FCS and seeded in 96-well plates at 100 µl per well. The plates were wrapped in plastic and incubated for three days, and the medium was then replaced with 180 µl per well of DMEM containing 2% FCS, 2 mM sodium pyruvate and 1% penicillin streptomycin (DMEM/2% FCS). The plates were wrapped in plastic and incubated for another two days. PDGF samples were diluted in 10 mM acetic acid/0.25% BSA to give an expected PDGF concentration of about 0.02–1.0 µg/ml. Samples (20 µl) were added to wells containing 180 µl of DMEM/2% FCS. The plates were swirled gently to mix, wrapped in plastic, and incubated for 18–22 hours. The media was then removed, and 100 µl of labeling mix (7 ml DMEM/5% FCS, 14 µl 1 µCi/µl [methyl-$^3$H]thymidine (Amersham International, Amersham, UK)) was added to each well. The plates were wrapped in plastic and incubated for 3 hours at 37° C., 5% $CO_2$. The cells were then detached from the wells by gently tapping the plates. Cells were harvested onto filters using a Betaplate cell harvester (LKB Wallac, Turku, Finland). The filters were dried at 50°–60° C. for 60 minutes and counted in a Betaplate 1205 scintillation counter (LKB Wallac) as described by the supplier. Results were compared to a standard curve generated using recombinant PDGF BB standards at 50, 25, 12.5, 6.3, 3.1, 1.6, 0.8, 0.4, 0.2 and 0 ng/ml final concentrations.

Mitogenic activity was used to determine shelf life. Assuming Arrhenius kinetics applies, shelf life was estimated as the time when 10% of PDGF-BB activity would be lost if held at 4° C. The zero-order rate constants were calculated from the percentage of initial PDGF-BB concentrations. In this way, the results from the three different PDGF-BB formulations could be directly compared. Non-specific derivitization, as determined by ion exchange chromatography, was used to support the findings from the mitogenic activity assays. As a final step, 6 and 8 week storage data, as determined by size exclusion chromatography, was compared by an analysis of variance. The mitogenic activity assay (data not shown) revealed that although a large deviation in the values was observed due to the nature of the assay, no significant loss of activity occurred. This indicates a commercially acceptable shelf life for PDGF-BB in the hydroxyethyl cellulose gel system.

Ion exchange chromatography was used to study the non-specific derivitization of PDGF-BB. Arrhenius kinetics applies well to the zero-order rate constants, $k_0$, obtained by linear regression ($R^2=0.96$). At 4° C. $k_0$ was estimated to equal 0.68% per week. Although the linear model does not apply well to the 4° C. data due to the relatively small changes observed, the estimated $k_0$ is in good accordance with the experimental value of 0.6% per week. The $k_0$ value at 40° C., 3.2% per week, is significantly higher than the findings in acetate buffer ($k_0=1.1$% per week) and pure water ($k_0=0.5$% per week). Thus, some interaction occurs between PDGF-BB and the constituents in the hydroxyethyl cellulose gel. Interaction of PDGF-BB is most likely with the HEC gel or impurities in it because prior work, as described in Example 2, failed to detect any degradation during 4 weeks at 40° C. From these findings, the calculated time to 10% non-specific derivitization at 40° C. is 14 weeks.

The data from size exclusion chromatography indicate no significant differences between the 5 temperatures tested ($p<0.185$). Thus, it is reasonable to assume that very little decomposition occurred during the 8 weeks of storage. Differences in the quantitative determination of PDGF-BB by the 3 methods used are due to differences in the PDGF-BB standards used to calibrate the assays.

The concentration of methyl paraben was evaluated by reverse-phase HPLC on a Hibar LiChrosorb RP-18 5 or 10µ column (Merck, Darmstadt, Germany). Elution was carried out at a flow rate of 1.5 ml/min. using a gradient of mobile phase A (0.01M triethylammonium phosphate buffer pH 4.0) and mobile phase B (20% 0.1M triethylammonium phosphate buffer pH 4.0 in acetonitrile) using the elution program shown in Table 3. The column was run at 40° C. using and injection volume of 50 µl. The eluant was monitored at 254 nm.

TABLE 3

| Time | % A | % B |
| --- | --- | --- |
| 0.00 | 63 | 37 |
| 7.00 | 63 | 37 |
| 14.00 | 56 | 44 |
| 19.00 | 56 | 44 |
| 21.00 | 63 | 37 |

To determine methyl paraben concentration, a standard solution of 15 mg p-hydroxybenzoic acid, 146 mg of methyl paraben and 20 mg of propyl parahydroxybenzoate was prepared in a total volume of 500 ml of water. The solution was filtered through a 0.22 µ filter. Three ml of this stock solution was diluted to 10 ml with water to produce the final standard solution. Fifty µl of the standard was fractionated by HPLC as described above. Approximate retention times for the standards were p-hydroxybenzoic acid, 2 minutes; methyl paraben, 5 minutes; and propyl parahydroxybenzoate, 15 minutes. Concentration (mg/ml) of methyl paraben was calculated as:

$$\frac{y \times A_{S,m} \times 20 \times 10}{A_{St,m} \times 1000} = \frac{y \times A_{S,m}}{A_{St,m} \times 5}$$

wherein
$A_{S,m}$=area of the methyl paraben peak in sample
$A_{St,m}$=area of the methyl paraben peak in standard
y=concentration of methyl paraben (mg/ml)
Methyl paraben concentration varied throughout the study but is within experimental error. No significant changes related to time or temperature were found to occur for pH or viscosity. Formation of polymers of PDGF was followed by size exclusion chromatography but none were detected (<5%).

EXAMPLE 6

Prediction of the Shelf Life of PDGF-BB at 4° C.

A second study was made to predict the shelf life of PDGF-BB formulations at 4° C. Briefly, PDGF-BB was formulated into an acetate buffered hydroxyethyl cellulose gel (HEC) containing methyl paraben as a preservative. The samples were held for 8 weeks at 4°, 15°, 25°, 30° and 40° C. Stability was followed by size exclusion chromatography (SEC) and supported by mitogenic activity assay and ion exchange chromatography (IEC) as described above. Additionally, gel viscosity, gel pH, and methyl paraben concentration were followed.

PDGF-BB at two concentrations, 500 $\mu$g/ml and 50 $\mu$g/ml, was formulated into 1.4% (w/v) HEC gels containing 0.2% (w/v) methyl paraben and 0.68% (w/v) sodium acetate. The samples were pH adjusted to 5.5 with HCl and stored as 1 ml aliquots in syringes (product no. 391593-001; plungers, no. 391592-001, Becton-Dickinson).

Determination of PDGF-BB derivative concentrations was made by cation exchange HPLC as described in Example 1. Determination of the concentrations of PDGF-BB and its polymers was made by size exclusion chromatography as described in Example 5. Samples held at 4° C. were tested at 0 and 8 weeks. Samples held at 15° C. and 20° C. were tested at 4 and 8 weeks. Samples held at 30° C. and 40° C. were tested at 2, 4, 6 and 8 weeks.

The appearance of the gel was determined macroscopically, pH was determined potentiometrically and rheology was determined viscosiometrically according to a second testing schedule. In this schedule, samples held at 4° C. were examined for the above three characteristics at 0 and 8 weeks. Samples held at 15° C. were tested at 8 weeks. Samples held at 20° C., 30° C. and 40° C. were tested at 4 and 8 weeks.

Shelf life was estimated using linear statistical analysis on the SEC data. Assuming Arrhenius kinetics applies, shelf life was estimated as the time when 10% of PDGF-BB activity would be lost if held at 4° C. During the study no change was observed in the appearance of the gels. Quantitative determination of PDGF-BB by SEC and mitogenic activity varied throughout the study by 10% and 50%, respectively, as a result of differences in PDGF-BB standards used in the calibration of the assays. Taking this difference into account, PDGF-BB concentrations as determined by SEC did not change during the 8 weeks of storage at temperatures below 25° C.

Zero-order rate constants were determined by calculating the PDGF-BB concentrations as a percentage of initial concentration and pooling the data from the 50 $\mu$g/ml and 500 $\mu$g/ml studies. Applying the Arrhenius equation to the rate constants obtained, we estimated a 10% loss of material in 132 weeks at 4° C. The IEC data, in which no degradation of PDGF-BB was observed, support this estimate.

The concentration of methyl paraben, as well as gel pH and viscosity, were within experimental error and were unaffected by incubation time and temperature.

EXAMPLE 7

Homogeneity of PDGF-BB in Gel

A study was performed to determine the homogeneity of PDGF-BB in hydroxyethyl cellulose (HEC) gels. Three 1-ml PDGF-BB gels, formed in syringes (product no. 391593-001; plungers, no. 391592-001, Becton-Dickinson), were made to concentrations of 50, 250 and 500 $\mu$g/ml in 1.6% (w/v) HEC. Additionally, each gel contained 0.2% (w/v) methyl paraben and 0.68% (w/v) sodium acetate. The pH of each gel was adjusted to 5.5 with HCl.

Prior to the assay, the gels were diluted 1:15 using the mobile phase buffers. The concentration of PDGF-BB was analyzed by cation exchange HPLC as described in Example 1.

Homogeneity was evaluated by determining the deviation between the putative PDGF-BB concentration in the gel and the measured concentration within the sample. Statistical analysis by ANOVA was made of the differences. Each gel filling was sampled at its start, middle and end. PDGF-BB concentrations in all gels (data not shown) were within ±10% and thus were within acceptable limits for homogeneity.

From the foregoing, it will be appreciated that, although specific embodiments of the invention have been described herein for the purposes of illustration, various modifications may be made without deviating from the spirit and scope of the invention. Accordingly, the invention is not limited except as by the appended claims.

We claim:

1. A composition comprising at least 90% pure platelet derived growth factor (PDGF) formulated in a carrier consisting essentially of hydroxyethyl cellulose (HEC) gel having a viscosity of about 200–30,000 cps, said composition having a concentration of PDGF between about 5 $\mu$g–5 mg PDGF per gram HEC gel.

2. The composition of claim 1 wherein the concentration of hydroxyethyl cellulose in said gel is between 1% and 5%, inclusive.

3. The composition of claim 1 wherein said PDGF comprises PDGF-BB.

4. The composition of claim 1 wherein said PDGF consists essentially of PDGF-BB.

5. The composition of claim 1 where in said PDGF is recombinant human PDGF-BB.

6. The composition of claim 1 wherein said PDGF is present at a concentration of about 5 $\mu$g to about 5 mg per gram of said gel.

7. The composition of claim 1 wherein said PDGF is present at a concentration of about 50–500 $\mu$g per gram of said gel.

8. The composition of claim 1, further comprising a preservative.

9. The composition of claim 8 wherein said preservative is methyl paraben.

10. The composition of claim 9 wherein said methyl paraben is present at a concentration of about 0.05% to about 1.0%.

11. The composition of claim 10 wherein said methyl paraben is present at a concentration of about 0.1% to 0.2%.

12. The composition of claim 1, further comprising ethanol.

13. The composition of claim 1, further comprising transforming growth factor alpha, transforming growth factor beta, epidermal growth factor, basic fibroblast growth factor, acidic fibroblast growth factor, platelet factor 4, insulin or a somatomedin.

14. A composition comprising at least 90% pure platelet derived growth factor-BB (PDGF-BB) formulated with methyl paraben in a hydroxyethyl cellulose (HEC) gel having a viscosity of about 200–30,000 cps, said composition having a concentration of PDGF between about 5 $\mu$g–5 mg PDGF per gram HEC gel.

15. A composition according to claim 14 wherein said PDGF-BB is recombinant human PDGF-BB.

16. A composition according to claim 14 wherein said PDGF-BB is present at a concentration of about 5 $\mu$g to 5 mg per gram of said gel.

17. A composition according to claim 14 wherein said PDGF-BB is present at a concentration of about 50–500 $\mu$g per gram of said gel.

18. A composition according to claim 14 wherein the concentration of hydroxyethyl cellulose in said gel is between 1% and 5%, inclusive.

19. A composition according to claim 14 wherein said methyl paraben is present at a concentration of about 0.05% to about 1.0%.

20. A composition according to claim 14 wherein said methyl paraben is present at a concentration of about 0.1% to 0.2%.

21. A composition consisting essentially of at least 90% pure PDGF formulated with 0.1% to 0.2% methyl paraben in a hydroxyethyl cellulose (HEC) gel having a viscosity of about 200–30,000 cps, said composition having a concentration of PDGF between about 50–500 $\mu$g PDGF per gram HEC gel.

22. A method of promoting wound healing in a warm-blooded animal comprising administering to said animal a therapeutically effective amount of at least 90% pure platelet derived growth factor (PDGF) formulated in a hydroxyethyl cellulose (HEC) gel having a viscosity of about 200–30,000 cps, said composition having a concentration of PDGF between about 5 $\mu$g–5 mg PDGF per gram HEC gel.

\* \* \* \* \*